US005741677A

United States Patent [19]
Kozlowski et al.

[11] Patent Number: 5,741,677
[45] Date of Patent: Apr. 21, 1998

[54] METHODS FOR MEASURING TELOMERE LENGTH

[75] Inventors: Michael R. Kozlowski; Karen R. Prowse, both of Palo Alto; Sy-shi Wang, Burlingame; Sharon Wong, San Jose; Nam Woo Kim, Sunnyvale; Richard Allsop, Menlo Park, all of Calif.

[73] Assignee: Geron Corporation, Menlo Park, Calif.

[21] Appl. No.: 479,916

[22] Filed: Jun. 7, 1995

[51] Int. Cl.$^6$ ............... C12P 19/34; C12Q 1/68; C07H 21/02; C07H 21/04
[52] U.S. Cl. ............ 435/91.2; 435/6; 435/174; 536/23.1; 536/24.3; 536/24.33
[58] Field of Search ............ 435/6, 174, 91.2; 536/23.1, 24.3, 24.33

[56] References Cited

U.S. PATENT DOCUMENTS

| | | |
|---|---|---|
| 4,737,454 | 4/1988 | Dattagupta et al. |
| 5,489,508 | 2/1996 | West et al. |

FOREIGN PATENT DOCUMENTS

| | | | |
|---|---|---|---|
| 2294322 | 4/1996 | United Kingdom | C12Q 1/68 |
| 9323572 | 11/1993 | WIPO | |
| 9408053 | 4/1994 | WIPO | |
| 95/13381 | 5/1995 | WIPO | C12N 15/54 |
| 95/13382 | 5/1995 | WIPO | C12N 15/54 |

OTHER PUBLICATIONS

Garagna et al. Chromosoma 103:685–693, 1995.
Burgtorf et al. Gene 137(2) 287–291, 1993.
Wright et al. NAR 23: 794–3795,1995.
Counter et al, PNAS 91: 2900–2904, 1994.
Ijdo, et al. (1991), "Improved telomere detection using a telomere repeat probe (TTAGGG)$_n$ generated by PCR," *Nucl. Acids Res.* 19 : 4780.
Weber et al. (1990), "Characterization and organization of DNA sequences adjacent to the human telomerase associated repeat (TTAGGG)$_n$," *Nucl. acids res. 18* : 3353–3361.
Feng et al., "The RNA Component of Human Telomerase", *Science* 269:1236–1241 (1995).
Farr et al., "Functional Reintroduction of Human Telomeres into Mammalian Cells", *PNAS* 88:7006–7010 (1991).
Brown et al., "Structure and Polymorphism of Human Telomere–Associated DNA", *Cell* 63:119–132 (1990).
Baird et al., "Mechanisms Underlying Telomere Repeat Turnover, Revealed by Hypervariable Variant Repeat Distribution Patterns in the Human Xp/Yp Telomere", *The EMBO Journal* 14:5433–5443 (1995).
Edwards et al., "Oligodeoxyribonucleotide Ligation to Single–Stranded cDNAs; a New Tool for Cloning 5' Ends of mRNAs and for Constructing cDNA Libraries by In Vitro Amplification", *Nucl. Acids Res.* 19:5227–5232 (1991).
Barany, "Genetic Disease Detection and DNA Amplification using Cloned Thermostable Ligase," *Proc. Natl. Acad. Sci. USA* 88:189–193 (1991).
Compton, "Nucleic Acid Sequence–Based Amplification", *Nature* 350:91–92 (1991).
Guatelli et al., "Isothermal, In Vitro Amplification of Nucleic Acids by a Multienzyme Reaction Modeled after Retroviral Replication", *Proc. Natl. Acad. Sci, USA* 87:1874–1878 (1990).

(List continued on next page.)

*Primary Examiner*—W. Gary Jones
*Assistant Examiner*—Dianne Rees
*Attorney, Agent, or Firm*—Lyon & Lyon LLP

[57] ABSTRACT

Methods are provided for the determination of telomere length. These methods can be used for diagnosis of cancer and the staging of cancer, and diagnosis of senecesence in cells. Also, the instant methods can be used to determine stages of diseases such as atherosclerosis or HIV infection, and can be used to diagnose infertility.

8 Claims, 12 Drawing Sheets

OTHER PUBLICATIONS

Walker et al., "Isothermal In Vitro Amplification of DNA by a Restriction Enzyme/DNA Polymerase System",*Proc. Natl. Acad. Sci. USA* 89:392–396 (1992).

Vaziri et al., "Loss of Telomeric DNA During Aging of Normal and Trisomy 21 Human Lymphocytes", *Am. J. Hum. Genet.* 52:661–667 (1993).

Counter et al., "Telomerase Activity in Normal Leukocytes and in Hematologic Malignancies", *Blood* 85:2315–2320 (1995).

Yamada et al., "Telomeric DNA in Normal and Leukemic Blood Cells", *J. Clin. Invest.* 95:1117–1123 (1995).

Allsopp et al., "Telomere length predicts replicative capacity of human fibroblasts," *Proc. Natl. Acad. Sci. USA* 89:10114–10118 (1992).

Blackburn et al., "Recognition and Elongation of Telomeres by Telomerase," *Genome* 31: 553–560 (1989).

Blackburn, "Structure and Function of Telomeres," *Nature* 350:572 (1991).

Blackburn, "The molecular structure of centromeres and telomeres," *Annual Reviews in Biochemistry* 53:163 (1984).

Cech, "Ribozymes and their medical implications," *J. of Amer. Med. Assoc.* 260:3030 (1988).

Cooke and Smith, "Variability at the telomeres of the human X/Y pseudoautosomal region," *Cold Harbor Symposia on Quantitative Biology* LI:213 (1986).

Cotten, "The in vivo application of ribozymes," *Trends in Biotechnology* 8:174–178 (1990).

Counter et al., "Stabilization of Short Telomeres and Telomerase Activity Accompany Immortalization of Epstein–Barr Virus–Transformed Human B Lymphocytes," *J. Virology* 68:3410–3414 (1994).

Counter et al., "Telomere shortening associated with chromosome instability is arrested in immortal cells which express telomerase activity," *EMBO J.* 11:1921–1929 (1992).

Counter et al., "Telomerase activity in human ovarian carcinoma," *Proc. Natl. Acad. Sci. USA* 91:2900–2904 (1994).

Eck and Nabel, "Antisense oligonucleotides for therapeutic intervention," *Current Opin. in Biotech* 2:897 (1991).

Gall, "Tying up loose ends," *Nature* 344:108 (1990).

Goldstein, "Replicative senescence: the human fibroblast comes of age," *Science* 249:1129 (1990).

Gottschling et al., "Position effect at *S. cerevisiae* telomeres: reversible repression of Pol II transcription," *Cell* 63:751 (1990).

Gray et al., "Cloning and expression of genes for the Oxytricha telomere–binding protein specific subunit interactions in the telomeric complex," *Cell* 67:807 (1991).

Greider, "Telomeres, telomerase and senescence," *Bioessays* 12:363 (1990).

Greider, "Chromosome first aid," *Cell* 67:645 (1991).

Greider et al., "Telomerase is Processive," *Molecular and Cellular Biology* 11:4572–4580 (1991).

Greider and Blackburn, "The telomere terminal transferase of tetrahymena is a ribonucleoprotein enzyme with two kinds of primer specificity," *Cell* 51:887–898 (1987).

Greider and Blackburn, "A telomeric sequence in the RNA of Tetrahymena telomerase required for telomere repeat synthesis," *Nature* 337:331–337 (1989).

Guo et al., "Interaction of the Dye Ethidium Bromide with DNA Containing Guanine Repeats," *Biochemistry* 31:2451–2455 (1992).

Ham and McKeehan, "Media and growth requirements," *Methods in Enzymology* LVIII:44 (1979).

Harley, "Telomere Loss: Mitotic Clock or Genetic Time Bomb?" *Nature* 256:271 (1991).

Harley, *Mutation Research* 256:271–282 (1991).

Harley et al., "The Telomere Hypothesis of Cellular Aging," *Experimental Gerontology* 27:375–382 (1992).

Harley et al., "Telomeres Shorten During Ageing of Human Fibroblasts" *Nature* 345:458 (1990).

Harrington and Greider, "Telomerase primer specificity and chromosome healing," *Nature* 353:451 (1991).

Hayflick et al., "The serial cultivation of human diploid cell strains," *Experimental Cell Research* 25:585 (1961).

Hendersen et al., "Telomere G–strand structure and function analyzed by chemical protection, base analogue substitution, and utilization by telomerase in vitro," *Biochemistry* 29:732 (1990).

Henderson et al., "Structure, Synthesis and Regulation of Telomeres," *Cancer Cells* 6:453–461 (1988).

Jankovic et al., "Telomere loss and cancer," *Nature* 350:197 (1991).

Kafatos et al., "Determination of nucleic acid sequence homologies and relative concentrations by a dot hybridization procedure," *Nucleic Acids Research* 7:1541–1552 (1979).

Klingelhutz et al., "Restoration of Telomeres in Human Papoillomavirus–Immortalized Human Anogenital Epithelial Cells," *Molecular and Cellular Biology* 14:961–969 (1994).

Lundblad and Szostak, "A mutant with a defect in telomere elongation leads to senescence in yeast," *Cell* 57:633 (1989).

Morin, "The human telomere terminal transferase enzyme is a ribonucleoprotein that synthesizes TTAGGG repeats," *Cell* 59:521 (1989).

Muller et al., "New telomere formation after developmentally regulated chromosomal breakage during the process of chromosome diminution in *Ascaris lumbricoides*" *Cell* 67:815 (1991).

Ohno, "Strict relationship between dialyzed serum concentration and cellular life span" *Mechanisms of Aging and Development* 11:179 (1979).

Olovnikov, "A theory of marginotomy," *J. Theoretical Biology* 41:181 (1973).

Shay et al., "Loss of telomeric DNA during aging may predispose cells to cancer (Review)," *Int'l J. Oncology* 3:559–563 (1993).

Smith et al., "Intraclonal variation in proliferative potential of human diploid fibroblasts: stochastic mechanisms for cellular aging," *Science* 207:82 (1980).

Starling et al., "Extensive telomere repeat arrays in mouse are hypervariable," *Nucleic Acids Research* 18:6881 (1990).

Strahl and Blackburn, "The effects of nucleoside analogs on telomerase and telomeres in Tetrahymena," *Nucleic Acids Research* 22:893–900 (1994).

Szostak, "The beginning of the ends," *Nature* 337:303 (1989).

Wang and Zakian, "Telomere–telomere recombination provides an express pathway for telomere acquisition," *Nature* 345:456 (1990).

Windle and McGuire, "Telomeres: the long and the short of it," *Proceedings of the American Association for Cancer Research* 33:594–595 (1992).

Yu et al., "In vivo alteration of telomere sequences and senescence caused by mutated *Tetrahymena* telomerase RNAs," *Nature* 344:126 (1990).

Yu et al., "Developmentally Programmed Healing of Chromosomes by Telomerase in Tetrahymena," *Cell* 67:823 (1991).

Zahler et al., "Inhibition of Telomerase by G-quartet DNA Structures," *Nature* 350:718-720 (1991).

| SLOT BLOT DATA | 1 BJ (PDL) | 2 T2AG3 INTENSITY | 3 BJ (AVERAGE T LENGTH) | 4 S2C (PDL) | 5 T2AG3 INTENSITY | 6 S2C (AVERAGE T LENGTH) | 7 pBLRep4 (pmol of T2AG3) | 8 T2AG3 INTENSITY |
|---|---|---|---|---|---|---|---|---|
| 1 | 27.5 | 357338 | 29.54 Kb | 30 | 286761 | 23.37 Kb | 0.06576 | 76976 |
| 2 | 28.6 | 346486 | 28.59 Kb | 39 | 258953 | 20.94 Kb | 0.132 | 155074 |
| 3 | 41.2 | 280452 | 22.82 | 44 | 262724 | 21.27 | 0.263 | 285200 |
| 4 | 46.6 | 293800 | 23.99 | 47 | 209496 | 16.62 | 0.394 | 402212 |
| 5 | 57.2 | 270484 | 21.95 | 53 | 159030 | 12.21 | | |
| 6 | 69.2 | 219510 | 17.49 | 62 | 157456 | 12.07 | | |
| 7 | 72.2 | 230505 | 18.45 | 69.2 | 166010 | 12.81 | | |
| 8 | 73.5 | 194970 | 15.35 | 71.2 | 150172 | 11.43 | | |
| 9 | 80 | 219628 | 17.50 | 73.2 | 174636 | 13.57 | | |

FIG. 3

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B |   | OVCAR 4 |   | OVCAR 3 |   | OVCAR 5 |   | OVCAR 8 |   | SK-OV-3 |   |   |
| C |   | 2 MG |   | 2 MG |   | 1 MG |   | 2 MG |   | 2 MG |   |   |
| D |   | 1 MG |   | 1 MG |   | 0.5 MG |   | 1 MG |   | 1 MG |   |   |
| E |   | 0.5 MG |   | 0.5 MG |   | 0.25 MG |   | 0.5 MG |   | 0.5 MG |   |   |
| F |   | 0.25 MG |   | 0.25 MG |   | 0.125 MG |   | 0.25 MG |   | 0.25 MG |   |   |
| G |   |   |   |   |   |   |   |   |   |   |   |   |
| H |   |   |   |   |   |   |   |   |   |   |   |   |

FIG. 10A.

OVCAR

| | 1 | 2 | 3 | 4 | 5 | 6 | 7 |
|---|---|---|---|---|---|---|---|
| | Sample | TRF (kb) | 2 ug | 1 ug | 0.5 ug | 0.25 ug | 0.125 ug |
| 1 | OVCAR 4 | 4.89 | 3235960 | 1600895 | 688627 | 262075 | |
| 2 | OVCAR 3 | 3.55 | 2701170 | 1326068 | 608269 | 247371 | |
| 3 | OVCAR 5 | 2.39 | | 851742 | 439777 | 211908 | 104927 |
| 4 | OVCAR 8 | 7.51 | 2901921 | 1406973 | 633572 | 267539 | |
| 5 | SK-OV-3 | 10.69 | 5612527 | 2880505 | 1359104 | 512160 | |

FIG. 11.

METHODS FOR MEASURING TELOMERE LENGTH

BACKGROUND OF THE INVENTION

1. Field of the Invention

The field of the present invention relates to methods and reagents for the measurement of telomere length.

2. Description of Related Art

The following is a general description of art relevant to the present invention. All art is incorporated by reference herein, and none is admitted to be prior art to the invention.

Normal human somatic cells (e.g., fibroblasts, endothelial, and epithelial cells) display a finite replicative capacity of 50–100 population doublings characterized by a cessation of proliferation in spite of the presence of adequate growth factors. This cessation of replication in vitro is variously referred to as cellular senescence or cellular aging, See, Goldstein, 249 *Science* 1129, 1990; Hayflick and Moorehead, 25 *Exp. Cell Res.* 585, 1961; Hayflick, ibid., 37:614, 1985; Ohno, 11 *Mech. Aging Dev.* 179, 1979; Ham and McKeehan, (1979) "Media and Growth Requirements", W. B. Jacoby and I. M. Pastan (eds), in: *Methods in Enzymology*, Academic Press, NY, 58:44–93. The replicative life span of cells is inversely proportional to the in vivo age of the donor (Martin et al., 23 *Lab. Invest.* 86, 1979; Goldstein et al., 64 *Proc. Natl. Acad. Sci. USA* 155, 1969; and Schneider and Mitsui, ibid., 73:3584, 1976), therefore, cellular senescence is suggested to play an important role in aging in vivo.

Cellular immortalization (the acquisition of unlimited replicative capacity) may be thought of as an abnormal escape from cellular senescence, Shay et al., 196 *Exp. Cell Res.* 33, 1991. Normal human somatic cells appear to be mortal, i.e., have finite replicative potential. In contrast, the germ line and malignant tumor cells are immortal (have indefinite proliferative potential). Human cells cultured in vitro appear to require the aid of transforming viral oncoproteins to become immortal and even then the frequency of immortalization is $10^{-6}$ to $10^{-7}$. Shay and Wright, 184 *Exp. Cell Res.* 109, 1989.

Telomeres, the TTAGGG repeat sequences capping the ends of chromosomes, have been shown to shorten during replicative aging of normal cells in vitro and in vivo. See, Harley et al., 345 *Nature* 458, 1990, which states that the amount and length of telomeric DNA in human fibroblasts decreases as a function of serial passage during aging in vitro, and possibly in vivo. The authors did not know whether this loss of DNA has a causal role in senescence. The enzyme telomerase can add TTAGGG repeats to the 3' end of telomeric DNA, thus extending the DNA and preventing shortening. Harley et al., supra, state:

"Tumour cells are also characterized by shortened telomeres and increased frequency of aneuploidy, including telomeric associations. If loss of telomeric DNA ultimately causes cell-cycle arrest in normal cells, the final steps in this process may be blocked in immortalized cells. Whereas normal cells with relatively long telomeres and a senescent phenotype may contain little or no telomerase activity, tumour cells with short telomeres may have significant telomerase activity. Telomerase may therefore be an effective target for anti-tumour drugs.

. . .

There are a number of possible mechanisms for loss of telomeric DNA during ageing, including incomplete replication, degradation of termini (specific or nonspecific), and unequal recombination coupled to selection of cells with shorter telomeres. Two features of our data are relevant to this question. First, the decrease in mean telomere length is about 50 bp per mean population doubling and, second, the distribution does not change substantially with growth state or cell arrest. These data are most easily explained by incomplete copying of the template strands at their 3' termini. But the absence of detailed information about the mode of replication or degree of recombination at telomeres means that none of these mechanisms can be ruled out. Further research is required to determine the mechanism of telomere shortening in human fibroblasts and its significance to cellular senescence." [Citations omitted.]

Michael D. West et al., entitled "Therapy and Diagnosis of Conditions Related to Telomere Length and/or Telomerase Activity," U.S. application Ser. No. 08/151,477, filed Nov. 12, 1993, and "Therapy and Diagnosis of Conditions Related to Telomere Length and/or Telomerase Activity," U.S. Pat. No. 5,489,508 issued Feb. 6, 1996, hereby incorporated by reference herein, generally describe art which relates to cellular senescence, and theories or hypotheses which explain such aging and the mechanisms by which cells escape senescence and immortalize.

The West et al. applications describe methods by which the length of telomeres can be measured. One method described involves the synthesis of DNA complementary to the telomeres of genomic DNA. The synthesized DNA can be labeled or unlabeled, and the length of this DNA can be determined by techniques known in the art.

Another method is known as terminal restriction fragment (TRF) analysis. In this method, the genomic DNA is digested with a restriction enzyme with a four-base recognition sequence (e.g. AluI, HinfI, MspI, RsaI, and Sau3A, used individually or in combination), which results in the production of short fragments of DNA, except for telomeric DNA which lacks these four base sequences. The DNA is then electrophoresed and a Southern blot performed by hybridizing the DNA to a radiolabeled probe, such as (TTAGGG)$_3$ or (CCCTAA)$_3$. The telomeric smears can then be visualized by autoradiography, and mean lengths of terminal restriction fragments calculated from densitometric scans using computer programs known in the art. Specific examples of this method are described in Examples 3 and 7 of the West et al. applications; this method is also described in Harley et al., 345 *Nature* 458, 1990, incorporated by reference herein.

The West et al. applications also describe measuring telomere length by the "anchored terminal primer" method, and by a modified Maxam-Gilbert reaction.

The West et al. applications explain that measurement of telomere length is useful in such things as diagnosis and the staging of cancer, and diagnosis of senecesence in cells. Also, measurement of telomere length can be used to determine stages of other diseases. For example, telomere length serves as a biomarker for alterations of cellular turnover in tissues associated with cardiovascular diseases, and thus can be used as a biomarker for the progression of atherosclerosis. Telomere length measurement is also useful as a means of determining replicative capacity of CD4$^+$ cells in a patient with HIV, thereby determining the stage of HIV infection in the patient. In addition, telomere length can be used to determine the efficacy of treatment with a telomere length modulating compound, and to discover agents which affect telomere lengths, or which affect the rate of telomere loss.

SUMMARY OF THE INVENTION

This invention concerns improved methods for the measurement of telomere length.

In a first aspect, the invention features a method for measuring the length of a telomere by contacting the telomere with a linker sequence under conditions in which the linker sequence is ligated or otherwise covalently bonded to the 3' end of the telomere. The telomere sequences are amplified by long PCR amplification with a first primer specific for the linker sequence and a second primer specific for a subtelomeric region of the chromosome. By "linker sequence" is meant a non-telomeric sequence. The linker sequence can be added by using terminal transferase and a specific dNTP (dCTP, dTTP or dATP), where the terminal transferase will add a long stretch of the specified dNTP that can be used as a priming site. The 3' linker can also be a non-telomeric oligonucleotide primer of specific length. The oligonucleotide can be added to the 3' end of the chromosome by RNA ligase that can blunt-end ligate single-stranded RNA or DNA molecules. An oligonucleotide that is complementary to the linker oligonucleotide can be used as a primer in the long PCR. This oligonucleotide, complementary to the linker oligonucleotide, is known as a "return primer".

By "subtelomeric region" is meant the portion of the chromosome which is 5' to the telomere sequence. This region is shown in FIG. 1. In this figure, P1 is the subtelomeric primer, P2 is the return primer, and the zig-zag line is the start of the telomere region. The black region represents the region complementary to the subtelomeric region.

By "long PCR" it is meant PCR amplification such as is described in Cheng, "Efficient PCR of Long Targets," *New Horizons in Gene Amplification Technologies: New Techniques and applications*; San Francisco, Calif. (1994), hereby incorporated by reference herein. In this procedure, the primer specific for a subtelomeric region is a site specific, and preferably chromosome specific, primer. Preferably, this primer should be complementary to a subtelomeric region that is present in most, if not all, human chromosome. Subtelomeric regions of many different chromosomes are known to those in the art. For chromosomes for which subtelomeric regions are not known, the regions can be determined in the art using known cloning and sequencing procedures. A specific example of a primer to a subtelomeric region is a primer based on telbam 8 probe, as described in Brown et al., Cell 63:119–132 (1990), hereby incorporated by reference herein. Telbam 8 probe is thought to be specific for chromosome 7q, which is believed by some in the art to be present in all human chromosomes. By incorporating the addition of a linker sequence at the 3' end of the chromosome, a return primer specific for the linker, and a primer complementary to the subtelomeric region of the chromosome (e.g., a primer based on a subtelomeric probe such as telbam 8), long PCR amplification can proceed. This method can be used to obtain an accurate and sensitive measurement of telomere length.

In a second aspect, the invention features a method for measuring telomere length by hybridizing an oligonucleotide probe to a telomere repeat sequence, and determining the amount of probe hybridized as a measure of telomere length.

In one preferred aspect, this method involves preparing DNA extracts of cells, incubating the extract with an oligonucleotide probe complementary to a telomere repeat sequence, and determining amount of probe bound as a measure of telomere length. In this method cells may be grown in a 24–96 well microtiter plate, and may be treated with test agents (e.g., synthetic compounds, fermentation extracts, nucleic acid preparations, and other agents known to those in the art) during culture. The method can be used to determine the effect of these test agents on telomere length. For example, the cells from each well can be harvested and the DNA prepared by a standard miniprep protocol. The DNA-containing solution can be passed through a DNA-binding filter. Preferably, the DNA-binding filter is nitrocellulose or Biodyne B membrane (as described below). Other binding filters are known in the art. The filter is then incubated with a labeled telomere-complementary oligonucleotide probe. The amount of probe bound to the filter can then be quantified, and the amount of probe bound can be determined as a measure of telomere length.

In a further aspect, this method can proceed in 96-well format. By using such a format, the method can be automated. Preferably, Pall SILENT MONITOR™ membrane bottomed test plates, having 0.45µ Biodyne B membrane bottomed wells are used.

Significantly, size separation of the DNA extracts is not required with this method, as is required in methods such as TRF analysis. Thus, the instant invention provides a rapid, high throughput, method for measuring telomere length.

The oligonucleotide probe can be composed of ribonucleotides, deoxyribonucleotides, or mixtures of both. Because human telomeres comprise repeats of sequence 5'-TTAGGG-3', the probe will be complementary to a sequence contained within a sequence of two or more such repeats, i.e., the probe will comprise a sequence such as 5'-CCCTAA-3', (for an RNA probe, 5'CCCUAA-3'), or 5'-CTAACC-3'. described in Prowse and Kowslowski, U.S. Application Ser. No. 08/288,501, filed Aug. 10, 1994, hereby incorporated by reference herein. A $^{32}$P-labeled riboprobe complementary to the telomeric DNA was prepared in advance using a Stratagene RNA transcription kit (HindIII-digested pBLRep4 DNA template, T3 RNA polymerase). Plasmid pBLRep4 comprises 100 of the telomeric repeat sequences 5'-TTAGGG-3' inserted into the EcoRI site of the Stratagene vector pBluescriptIISK+. To stop the reaction, 1 µl of RNase-free DNase was added and the mixture incubated at 37° C. for 15 min. The reaction was then PCIA (phenol, chloroform, isoamyl alcohol) extracted (using an equal volume), and ⅒ volume of 3M sodium acetate and 2.5 volumes of ethanol were added to precipitate the RNA probe. The RNA was collected by centrifugation for 10 min. and dissolved in 100 µl TE buffer in DEPC-treated $H_2O$. The probe can be prepared by a variety of methods other than the method used in this example. For instance, one can use a commercially-available oligonucleotide synthesizer to prepare an oligonucleotide probe complementary to telomeric DNA. As telomerase mediates the synthesis of telomeric repeat units of the sequence 5'-TTAGGG-3', deoxyribo- or ribo-oligonucleotide probes complementary to the repeat unit or any portion of a multiple-repeat sequence can also be used as a probe in this method. In similar fashion, a variety of labels, including radioactive and non-radioactive labels, can be employed in the method. Typically, the oligonucleotide will be 8 or more nucleotides in length, preferably 12 to 15, or even 20 or more nucleotides in length. In a preferred method, a riboprobe is used. By "riboprobe" it is meant a probe comprised of ribonucleotides.

In an additional preferred aspect, the invention features an improved method of measuring telomere length by binding the genomic DNA to a solid phase, and hybridizing the bound DNA with a labeled probe. Preferably, the DNA will be bound to a solid phase by slot-blotting. Slot blotting is described in Kafatos et al, *Nucl. Acid Res.* 7:1541–1552; 1979, hereby incorporated by reference herein. Slot blotting is a method for rapidly determining the relative concentrations of nucleic acids in a mixture. In this method, samples of nucleic acid are spotted on a single nitrocellulose filter (e.g., Schleicher & Schuell™ nitrocellulose filter) and the filter is hybridized with a labeled oligonucleotide probe. The extent of hybridization of the probe with each of the nucleic acid dots is evaluated semi-quantitatively by comparing to a standard.

Preferably, the DNA can be sheared by digesting with restriction endonucleases, or by sonicating, or other methods known to those in the art. Such shearing may potentially improve the hybridization kinetics of the method.

This method can be used to rapidly and easily measure telomere length. Using this method, relative values for telomere intensity can be obtained within three days, in contrast to methods such as mean TRF analysis which take at least one week. Further, with the instant method it is not necessary to size separate the nucleic acid being analyzed (i.e., the instant method does not require the step of running the samples on a gel). This method gives a sensitive comparison of samples, and that the background from hybridization is minimal. The instant method is not significantly affected by moderate DNA degradation (which occurs frequently during storage or handling of the DNA). Further, problems which can occur in methods which require the running of gels (e.g., DNA trails caused by the trapping of some DNA in the wells, or the appearance of modes from the same DNA sample) are avoided with this method. In addition, this method is a high-throughput assay, as one blot can hold up to 72 or more samples.

These improved methods of measuring telomere length can be used as described above, to diagnose senescence in cells, and to determine disease states. The measurement of telomere length can also be used to diagnose fertility problems. Telomere length was measured in sperm cells from both fertile and infertile males. The sperm cells from infertile males had significantly shorter telomeres than the sperm cells of the fertile males. These data suggest that telomere length measurement could be used as a diagnostic of fertility problems.

Other features and advantages of the invention will be apparent from the following description of the preferred embodiments thereof, and from the claims.

DESCRIPTION OF THE PREFERRED EMBODIMENTS

Brief Description of Drawings

FIG. 3 shows tables displaying the results obtained using the slot-blotting method. These tables show that telomere length and T2AG3 (TTAGGG) signal intensity decrease with increased population doubling levels (PDL), and show that T2AG3 signal intensity increases with telomere length. These results are shown for both BJ cells (human foreskin fibroblast) and for S2C cells (human skin fibroblast). These cells, are publicly available through the American Type Culture Collection (ATCC). However, these exemplified cells are not essential to the method, as any cell type could be used with this method. In addition, these tables show the increase in T2AG3 signal intensity with increase in concentration of pBLRep4. pBLRep4 is a plasmid, publicly available through ATCC, which comprises 100 of the telomere repeat sequences 5'-TTAGGG-3' inserted into the EcoRI site of the Stratagene vector pBluescriptIISK+. As shown in this figure, this plasmid can be used to produce a standard curve by providing known amounts of telomere repeat sequence. Column 1 shows the population doubling level (PDL) for the BJ cells. Column 2 shows the T2AG3 intensity for BJ cell telomeres hybridized to telomere probes by means of the slot blotting method. Column 3 shows the average telomere length of the BJ cells, measured by TRF analysis. Column 4 shows the population doubling level (PDL) for the S2C cells. Column 5 shows the T2AG3 intensity for S2C cell telomeres hybridized to telomere probes by means of the slot blotting method. Column 6 shows the average telomere length of the S2C cells, measured by TRF analysis. Column 7 shows the amount of T2AG3 repeat sequence (in pmol) in the pBLRep4 standards. Column 8 shows the T2AG3 intensity for pBLRep4 hybridized to telomere probes by means of the slot blotting method.

FIG. 4 represents the standard curve of pBLRep4, and shows that the signal increases in a linear manner with increased concentration of pBLRep4 (T2AG3). FIGS. 5 and 6 show that T2AG3 intensity decreases with increased PDL in BJ cells and S2C cells. This is consistent with the decrease in telomere length seen with increased PDL in these cells (see FIG. 3).

FIGS. 10–12 show results obtained using the telomere probe method described above to compare telomere length of samples. FIGS. 10A and 10B show the placement of samples (as described below in Example 2) in a 96-well plate, and the scan of these samples after hybridization with the riboprobe. FIG. 11 is a table of the results of the scan, and the TRF lengths of the samples, measured by conventional TRF analysis. This figure shows that the signal intensity was higher in the samples with longer TRFs, and that this was consistent for all concentrations. FIG. 12 shows a graphic representation of these results.

EXAMPLES

Figure 1:
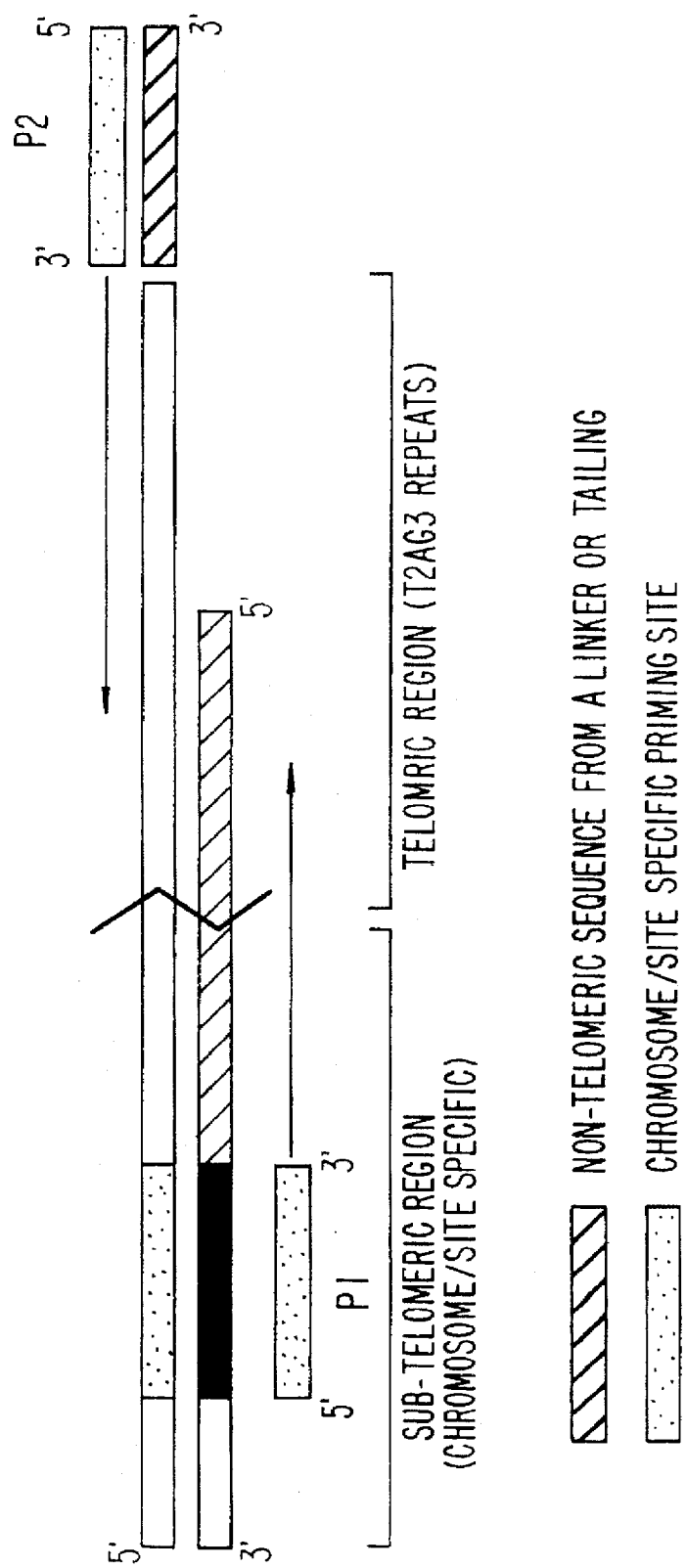
FIG. 1 shows an example of long PCR-based telomere measurement.
Figure 2A:
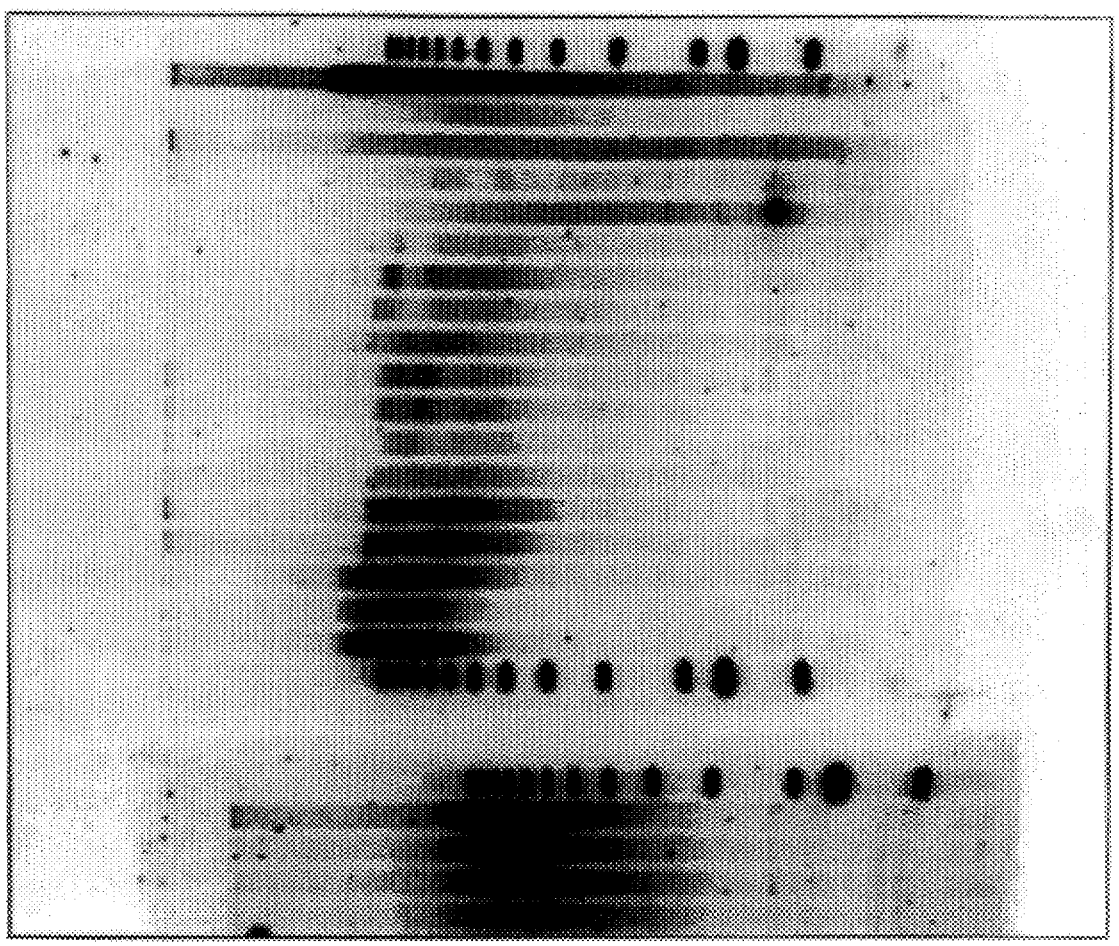
FIGS. 2A and 2B shows a comparison of a gel obtained from telomere measurement using standard TRF analysis (FIG. 2A) and a scan of a blot obtained using the slot-blotting method described above (FIG. 2B).
Figure 2B:
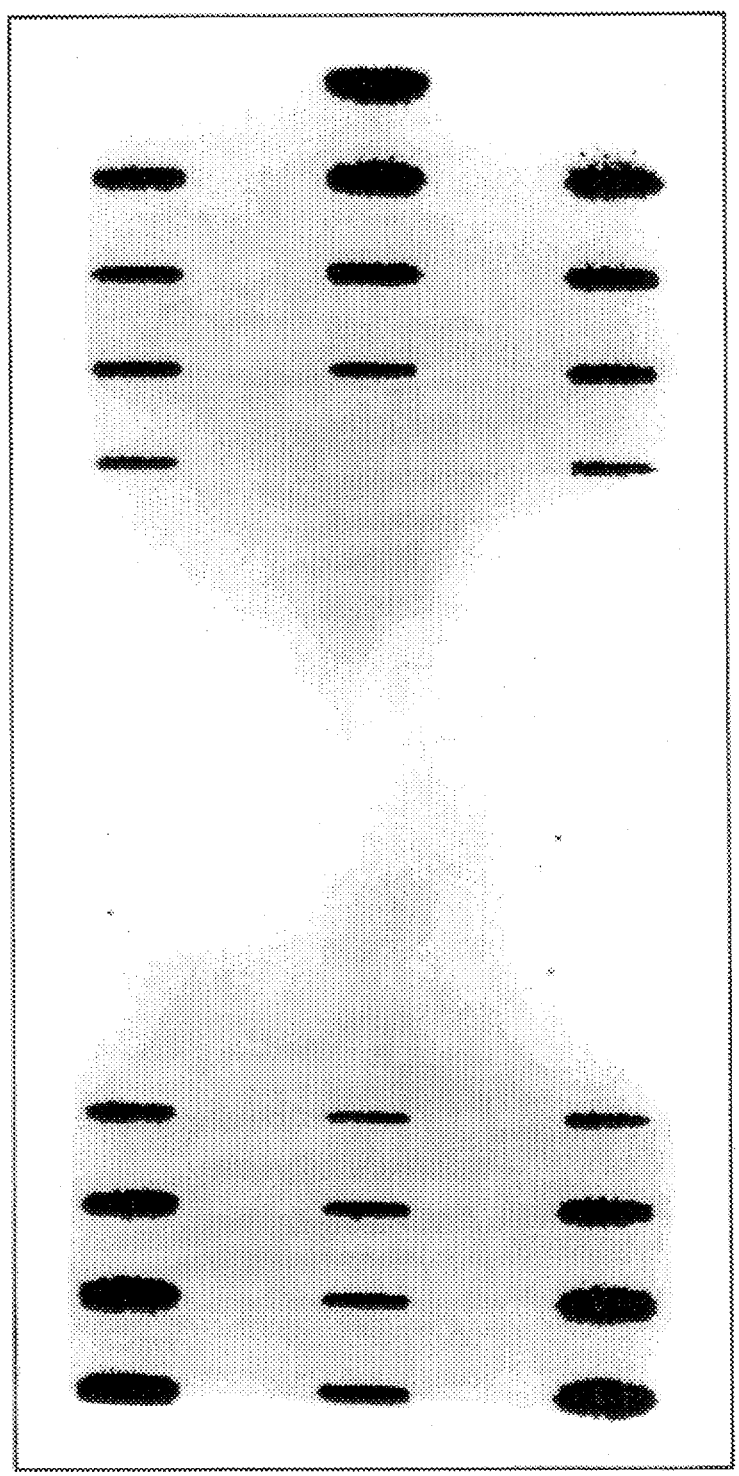
Figure 4:
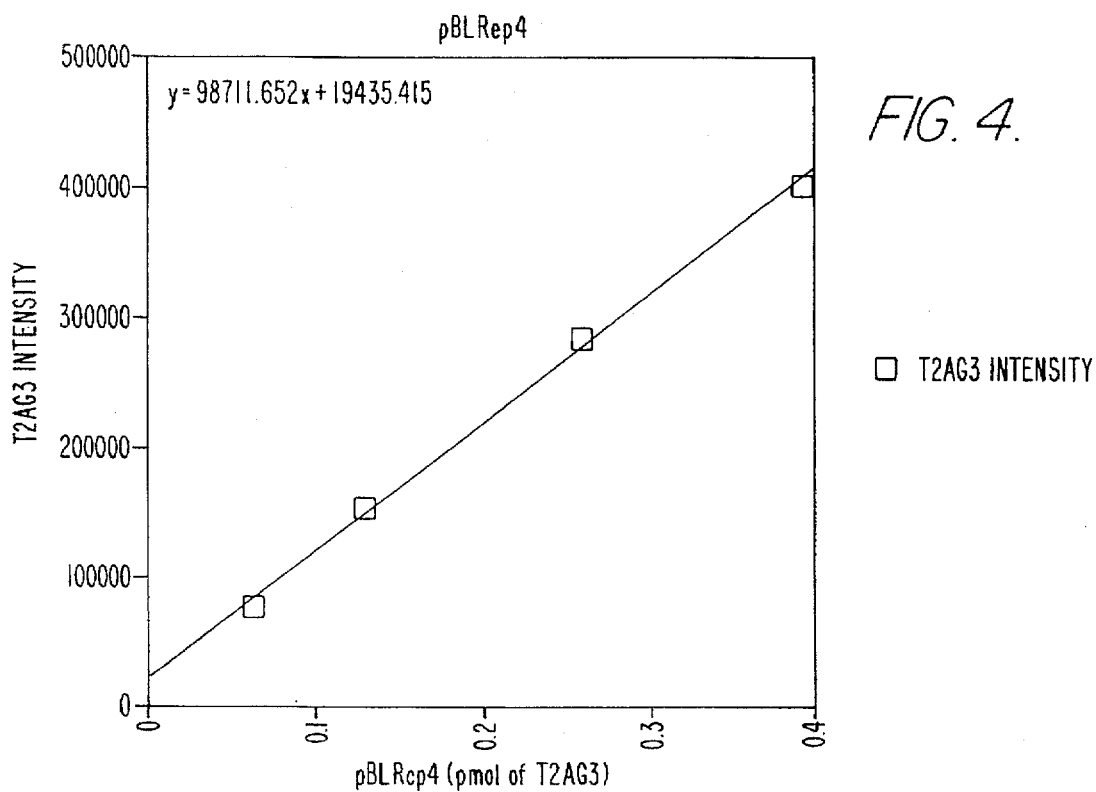
FIGS. 4–6 show graphic representation of results obtained using the slot-blotting method.
Figure 5:
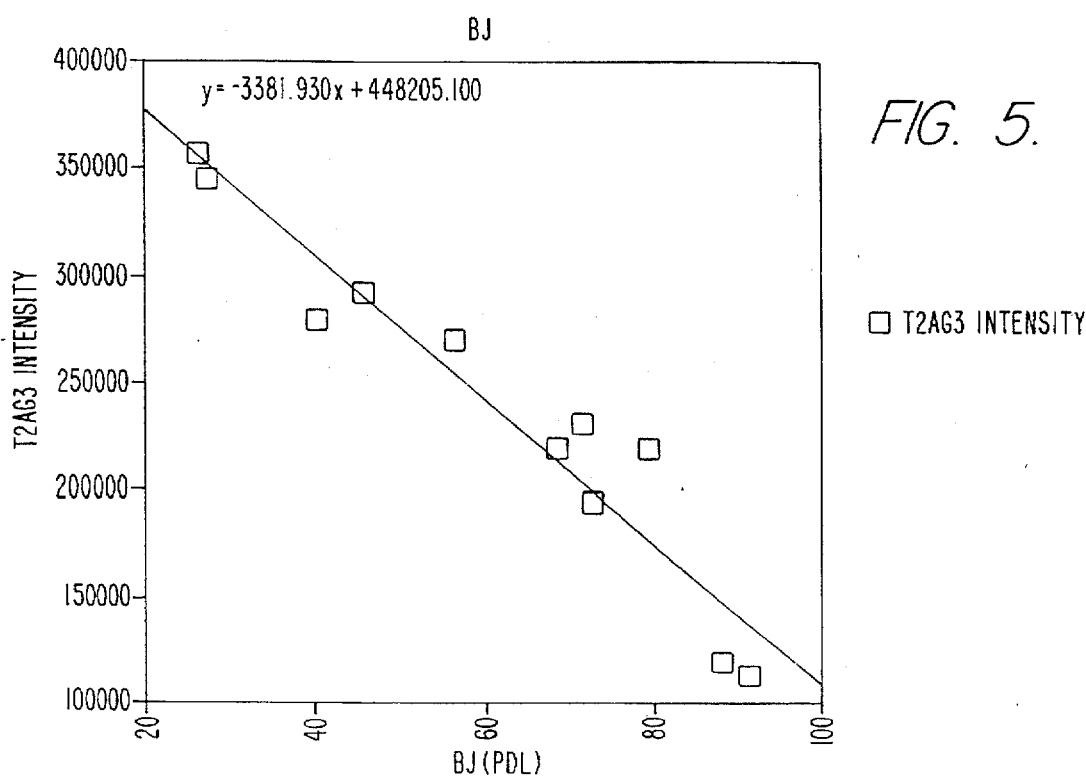
Figure 6:
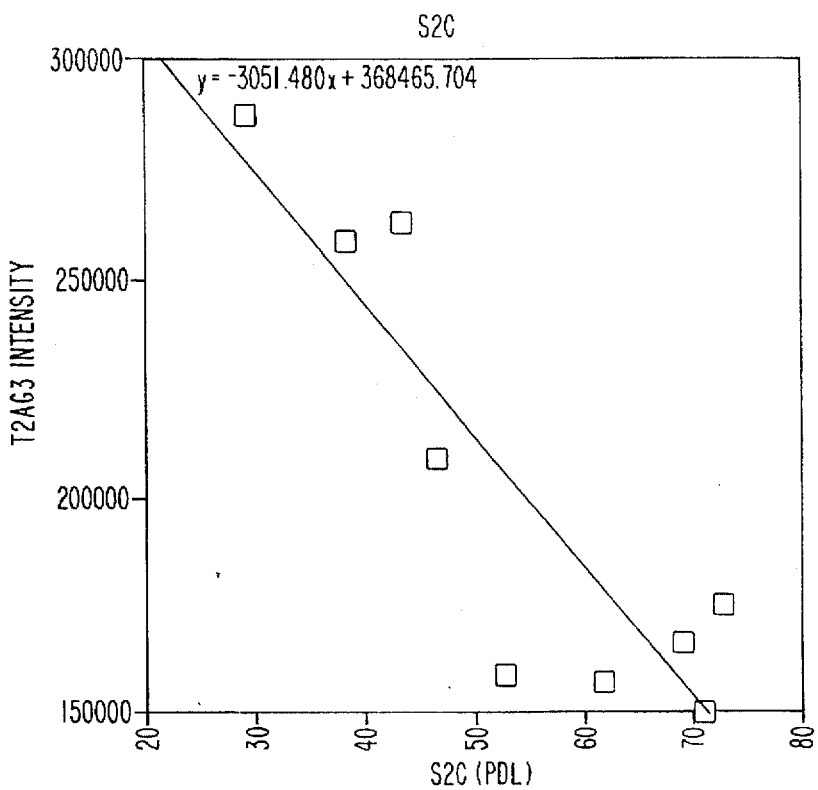

The following are examples of specific aspects of the invention to illustrate this invention to those in the art. These examples are not limiting of the invention, but provide an indication of specific methodology useful in practice of the invention.

EXAMPLE 1

Slot Blot

The slot-blotting method was carried out as described below to determine telomere length of samples. These cells and plasmids are not limiting in this invention.

Method 1.5 µg of total genomic DNA from BJ cells (human foreskin fibroblast) and from S2C (human skin fibroblast) at different population doubling levels ("PDL") was digested with both EcoRI and HindIII overnight.

1.25 μg of plasmid pBLRep4 (which is equivalent to 52.6 pmol of T2AG3 repeat) was digested with XbaI. This was used as a standard.

1.5 μg of Lambda phage DNA was digested with both Sau3A and HindIII, to be used as a negative control.

The digested DNA was purified by phenol/chloroform extraction followed by ethanol precipitation, then was resuspended in 100 μl of 1×TE buffer. 200 μl of 5×SSC was added to bring the volume to 300 μl, and the solution was mixed thoroughly.

A Schleicher & Schuell Minifold II™ apparatus was used to do the slot blotting. The blotting paper and nitrocellulose paper was wet with 5×SSC, and each slot was rinsed with 300 μl 5×SSC.

The digested DNA samples were then loaded onto the designated slots.

To generate a standard curve on the blot, the digested plasmid pBLRep4 was diluted at a serial ratio, and 0.009375 μg, 0.00625 μg, 0.003125 μg, and 0.0015625 μg was loaded onto separate slots.

A vacuum was used to filter all liquid through the blot, retaining the DNA on the blot. The nitrocellulose was then removed and placed on a piece of 3 MM paper and air dried for 30 minutes.

The DNA was denatured by placing the blot on a stack of 3 MM paper soaked with 0.5N NaOH+1.5M NaCl for 30 minutes. The DNA was then neutralized by placing the blot on 3 MM paper soaked with 0.5 M Tris at pH 7.4, 1.5M NaCl for 30 minutes. The DNA was cross-inked to the blot with UV STRATALINKER 1800™ (Stratagene).

The blot was prehybridized with prehybridization buffer (15 ml of 5×SSC, 5×Denhardt's Solution, 0.02M Phosphate pH 6.5, 0.1 mg/ml Salmon Sperm DNA, 0.5% SDS, 50% Formamide) for 2 hours.

The blot was then hybridized with 15 ml prehybridization buffer plus $^{32}$P labeled T2AG3 18 mer probe (1 million cpm/ml), and incubated overnight at 37° C.

The blot was washed with 500 ml 1×SSC, 0.1% SDS once for 10 minutes at room temperature, then twice with 500 ml 0.1×SSC, 0.1% SDS at 37° C. for 20 minutes.

The blot was exposed in a PhosphoImager™ detector (Molecular Dynamics) overnight. The intensity of the hybridization was then analyzed.

Results

The signal intensity of T2AG3 hybridization in cells of different PDL was converted to a relative number that reflected the average length of telomeres according to the standard curve (pBLRep4). The slot blotting method showed the decrease in average telomere length with increased PDL. These results are consistent with the TRF values determined by conventional methods. These results are shown in FIGS. 3–6.

EXAMPLE 2

Telomere Specific Probe

The following is a description of a telomerespecific probe method, as described above, which can be used to measure telomere length.

Method 2 six-well plates of 293 cells (available through ATCC) at 100,000/well and 1 six-well plate of 293 cells at 75,000/well were used. The wells of the plates were washed twice with cold 1×PBS buffer. 1.5 ml extraction buffer (10 mM Tris, pH 8.0, 0.1M EDTA, pH 8.0, 0.1M NaCl, 0.5% SDS, 100 μg/ml proteinase K) was added to each well, and the samples were incubated at 50° C. for 3–16 hours, adding an additional dose of proteinase K after 1 hour. Other extraction steps, e.g., digesting with EcoRI/HindIII and/or phenol:EtOH extraction could also be used.

15 μl/well RNase, DNase-free, was added, and samples were incubated for 1 hour. Cells were scraped and transferred to tubes. The samples were then heated at 65° C. for 10–20 minutes. The DNA was removed with a glass pasteur pipet, and resuspended in 100 μl TE buffer.

150 μl, 75 μl, 37.5 μl, and 18.75 μl, of the resuspended DNA was spotted into 96-well u-bottom plates. 160μl 0.5M NaOH/12.5 mM EDTA was added, and the contents were transferred to 96-well filter plates. The filters were vacuumed, adding 160 μl 0.4M NaOH, then washed in 2×SSC and laid flat to dry.

The filters were then hybridized with 50μl $^{32}$P-UPT labeled riboprobe (comprising repeats of the sequence 5'-CCCTAA-3', as discussed above) overnight at 65° C. The filters were washed in 1×SSC/0.1% SDS 4–5×, and were exposed for at least 1 hour in a PhosphoImager™ (Molecualar Dynamics) cassette and scanned.

Results

Figure 9:
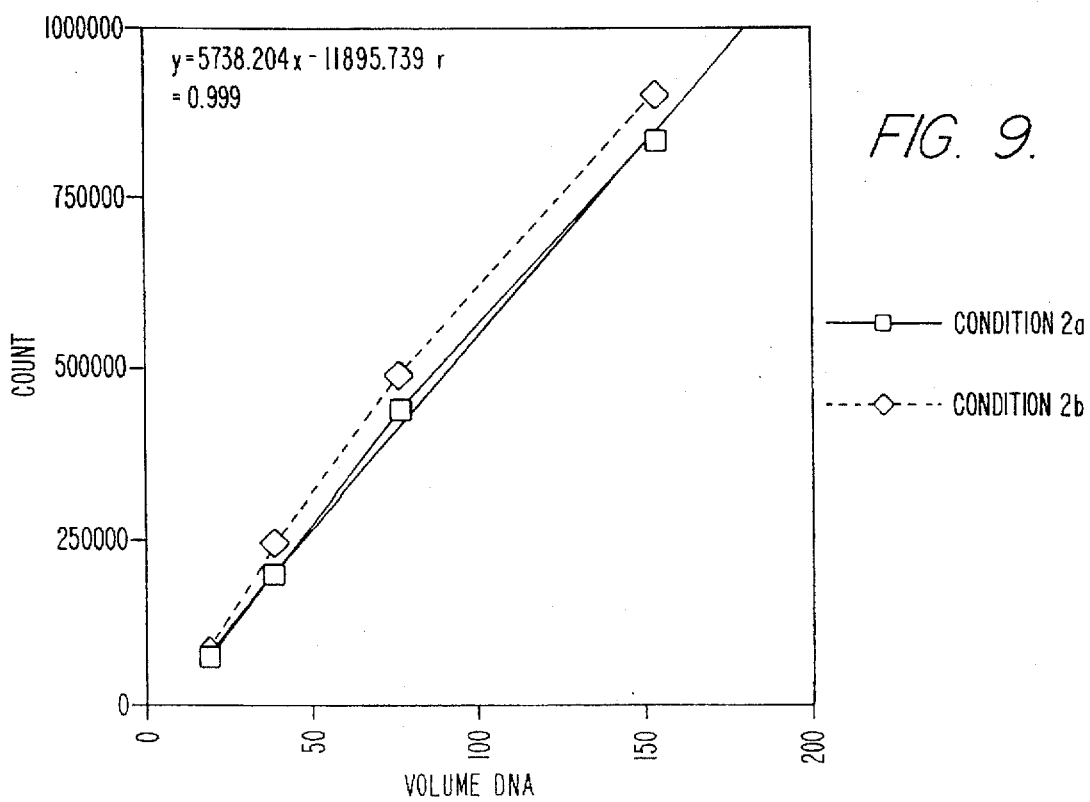
FIGS. 8–9 show graphical representations of the results obtained when different amounts of DNA were probed with the telomere-specific probe. These graphs show that increased signal was produced with increased amount of DNA.
Figure 7:
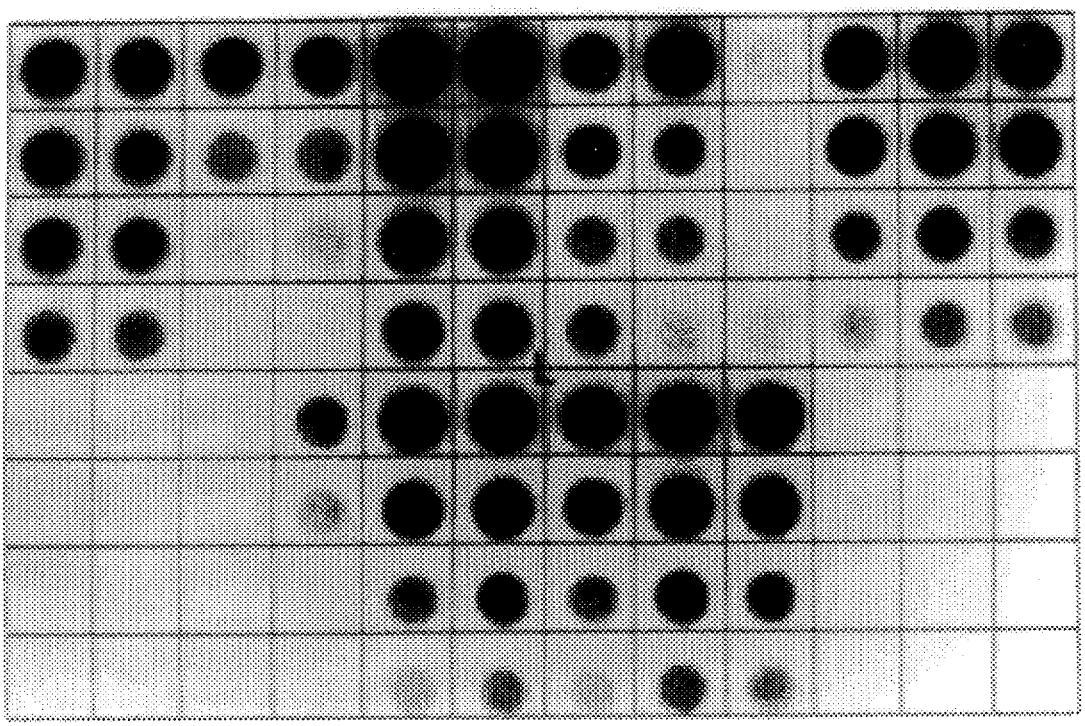
FIG. 7 shows a scan of a 96-well plate in which DNA samples were probed with a telomere-specific riboprobe as described above.
Figure 8:
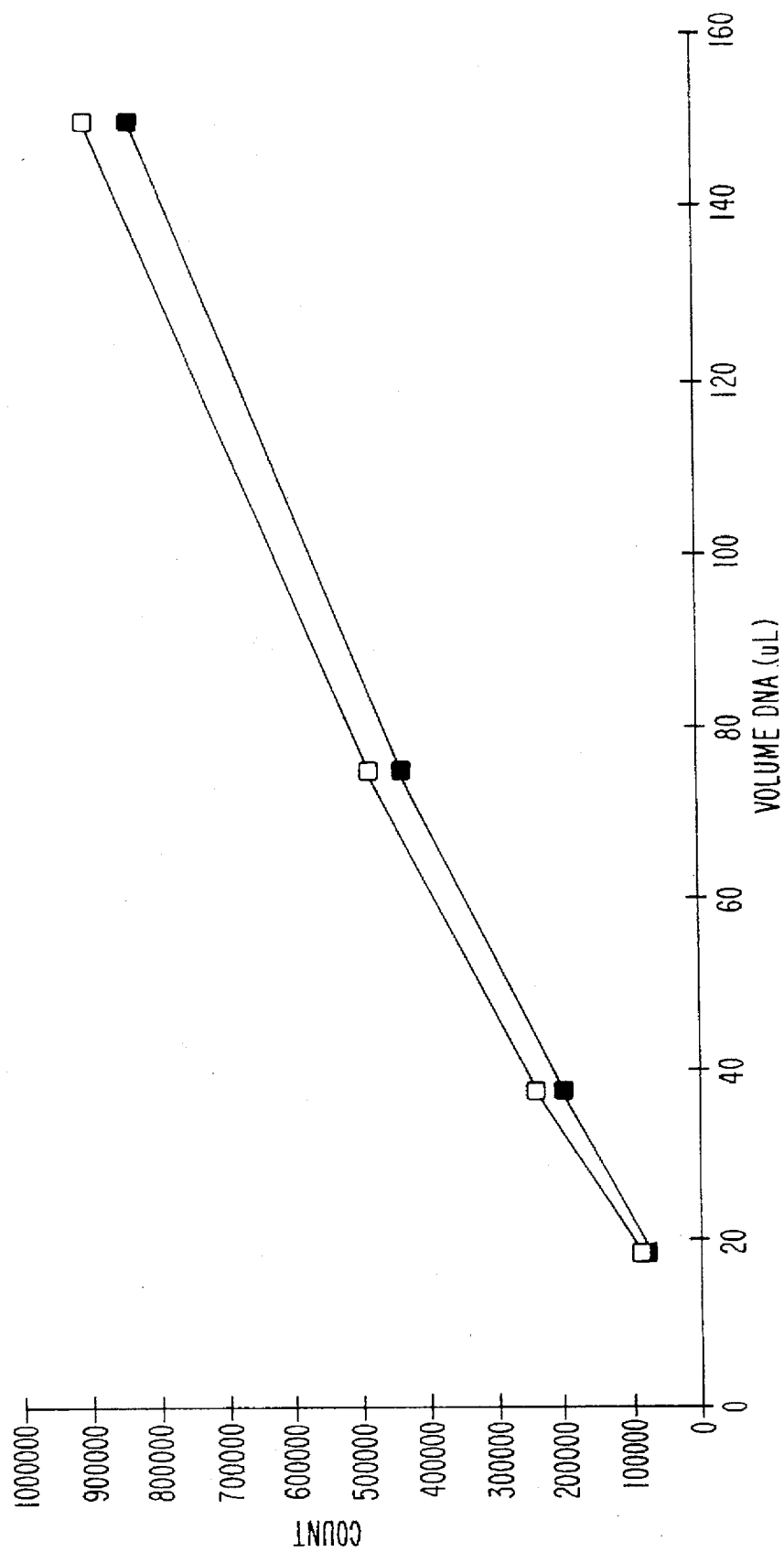

FIGS. 8–9 show the results of a method as described above. These figures show that the signal increases with the amount of DNA.

Figure 10B:
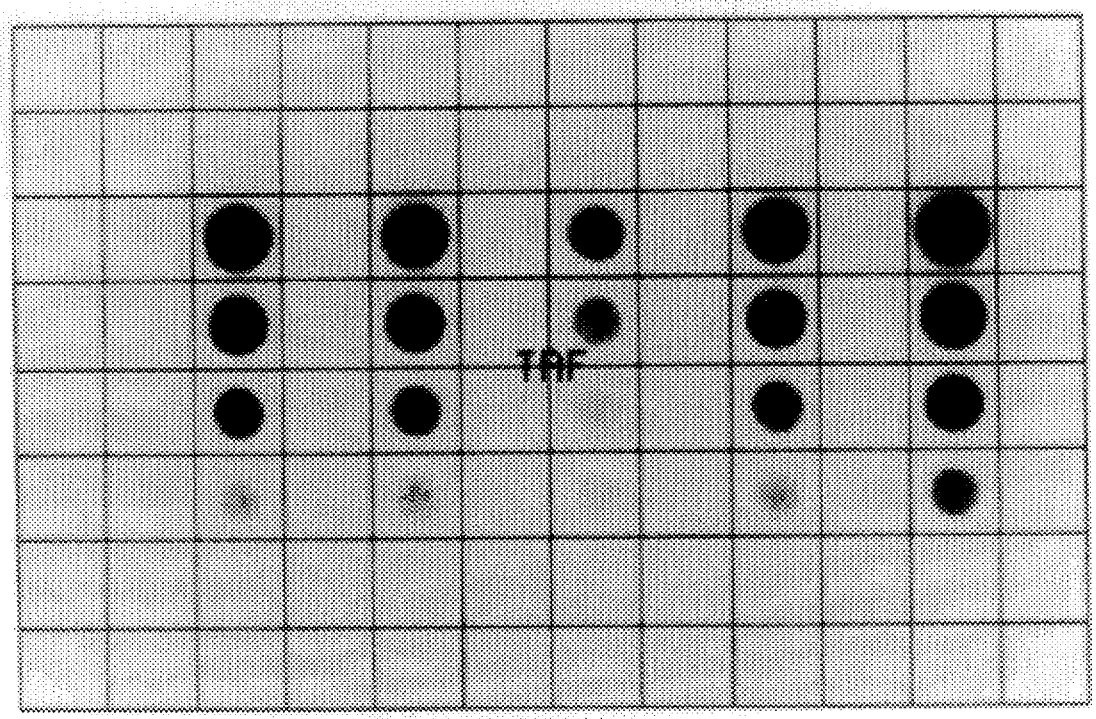
Figure 12:
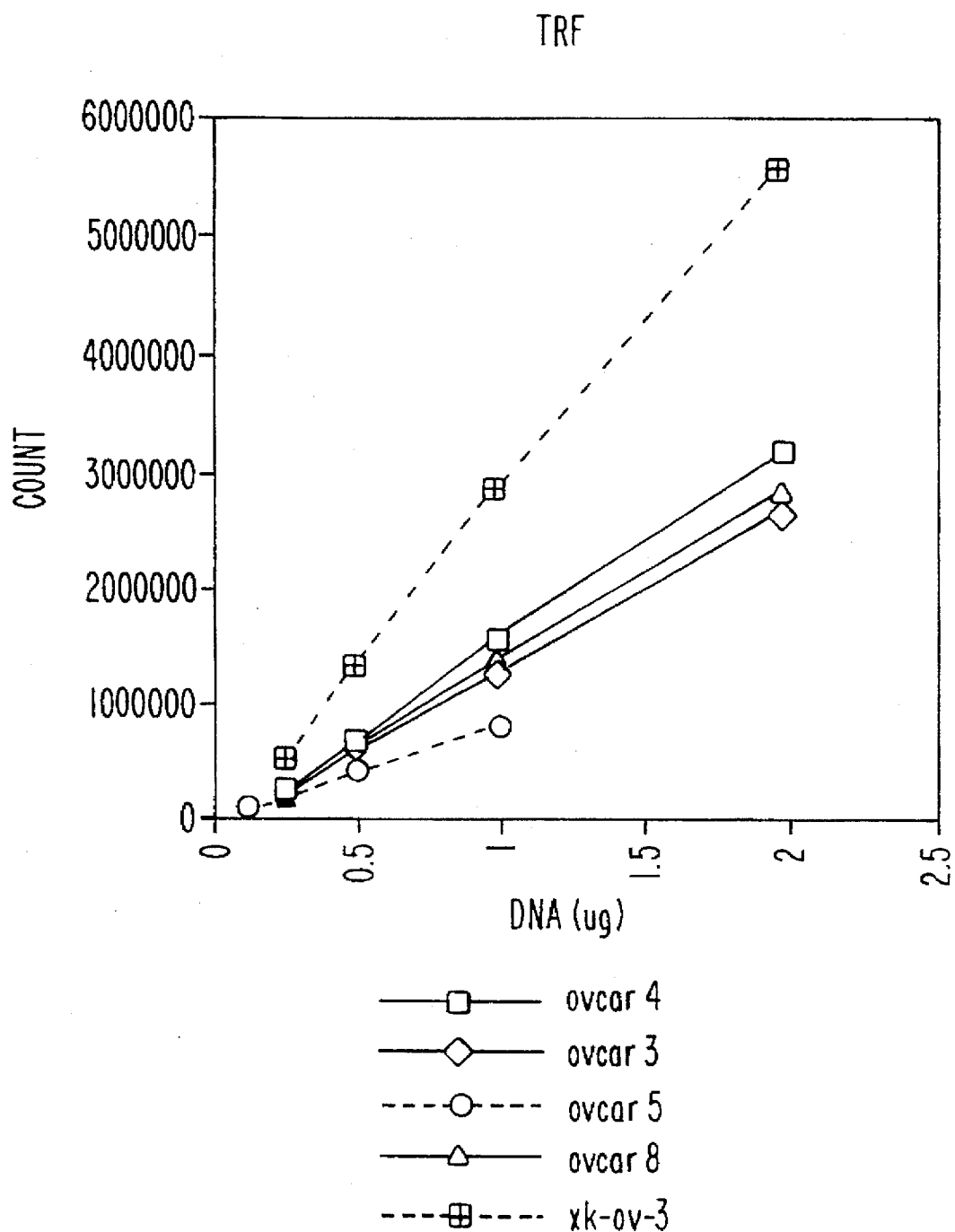

Using a method as described above, samples of known DNA concentrations (OVCAR 4, OVAR 3, OVAR 5, OVAR 8, and SK-OV-3, as shown in FIGS. 10 and 11) were analyzed to determine whether this method could be used to detect relative differences in telomere length. Telomere lengths of these samples were measured using mean TRF analysis, as discussed above. FIGS. 10–12 show that signal increased relative to telomere length. For example, SK-OV-3 cells, had the highest TRF of the samples (10.69 kb) and also had the strongest signal at each concentration.

The foregoing examples describe various aspects of the invention. The examples are not intended to provide an exhaustive description of the many different embodiments of the invention encompassed by the following claims.

We claim:

1. A method for measuring an average length of telomeres in a sample comprising a cell or tissue, said method comprising steps of:

(a) contacting said telomeres with an oligonucleotide linker under conditions such that said linker is covalently linked to a 3' end of said telomeres;

(b) amplifying with a first primer complementary to said oligonucleotide linker and a second primer complementary to a subtelomeric region of a chromosome under conditions in a reaction mixture such that said first and second primers hybridize specifically to said linker and subtelomeric region, respectively, and are extended by a polymerase, thereby forming first and second primer extension products; and (c) measuring an amount by which said first and/or second primer has been extended to form said extension products or duplex nucleic acids comprising said first and second primer extension products to determine an average telomere length.

2. A method of diagnosing infertility in males, wherein said method comprises steps of:

(a) measuring telomere length in a sperm sample from a subject to obtain a measured telomere length, by:

(i) contacting telomeres in said sperm sample with an oligonucleotide linker under conditions such that said linker is covalently linked to a 3' end of said telomeres;

(ii) amplifying with a first primer complementary to said oligonucleotide linker and a second primer complementary to a subtelomeric region of a chromosome under conditions such that said first and second primers hybridize specifically to said linker and subtelomeric region, respectively, and are extended by a polymerase, thereby forming first and second primer extension products; and (iii) measuring an amount by which said first and/or second primer has been extended to form said first and second primer extension products or duplex nucleic acids comprising said extension products to determine an average telomere length;

(b) comparing said measured telomere length to a control telomere length obtained by measuring telomere length in a sperm sample obtained from a fertile male; and (c) correlating a decreased telomere length in said sample from said subject, as compared to said control telomere length, with infertility.

3. The method of claim 1, wherein said telomere length determined in step (c) is correlated to a condition or stage of a condition associated with an increased rate of proliferation by comparing said telomere length to a control telomere length obtained by measuring telomere length in a sample obtained from a control subject, and correlating a decrease in telomere length relative to said control telomere length with said condition or stage of a condition.

4. The method of claim 1, wherein step (b) comprises steps of:

(1) heating said reaction mixture to denature duplex DNA molecules; and (2) cooling said reaction mixture to a temperature at which complementary nucleic acids can hybridize and said primers can extend.

5. The method of claim 1, wherein said telomere length is correlated to proliferative capacity of a cell in said sample.

6. The method of claim 4, wherein said heating and cooling steps are repeated and said first and second primers are present in amounts sufficient for formation of primer extension products after each heating step.

7. The method of claim 3, wherein said condition is atherosclerosis.

8. The method of claim 3, wherein said condition is HIV-infection.

* * * * *